US012109054B2

United States Patent
Karnick et al.

(10) Patent No.: US 12,109,054 B2
(45) Date of Patent: Oct. 8, 2024

(54) METHOD AND APPARATUS FOR FLAT PANEL COMPUTED TOMOGRAPHY

(71) Applicant: KA IMAGING INC., Waterloo (CA)

(72) Inventors: Amol S. Karnick, Oakville (CA); Karim S. Karim, Waterloo (CA)

(73) Assignee: KA IMAGING INC., Waterloo (CA)

( * ) Notice: Subject to any disclaimer, the term of this patent is extended or adjusted under 35 U.S.C. 154(b) by 224 days.

(21) Appl. No.: 17/612,803

(22) PCT Filed: May 22, 2020

(86) PCT No.: PCT/CA2020/050693
§ 371 (c)(1),
(2) Date: Nov. 19, 2021

(87) PCT Pub. No.: WO2020/232558
PCT Pub. Date: Nov. 26, 2020

(65) Prior Publication Data
US 2022/0240875 A1    Aug. 4, 2022

Related U.S. Application Data

(60) Provisional application No. 62/851,894, filed on May 23, 2019.

(51) Int. Cl.
*A61B 6/06*          (2006.01)
*A61B 6/03*          (2006.01)
(Continued)

(52) U.S. Cl.
CPC .............. *A61B 6/06* (2013.01); *A61B 6/032* (2013.01); *A61B 6/08* (2013.01); *A61B 6/4014* (2013.01); *A61B 6/4078* (2013.01); *A61B 6/4233* (2013.01)

(58) Field of Classification Search
CPC .. A61B 6/06; A61B 6/032; A61B 6/08; A61B 6/4014; A61B 6/4078;
(Continued)

(56) References Cited

U.S. PATENT DOCUMENTS

| 4,958,365 A * | 9/1990 | Sohval ................... H01J 35/24 |
| | | 378/119 |
| 2006/0056581 A1* | 3/2006 | Hoffman ................ A61B 6/032 |
| | | 378/19 |

(Continued)

FOREIGN PATENT DOCUMENTS

| JP | 2009082173 A | 4/2009 |
| JP | 2011255098 A | 12/2011 |
| WO | 2018/108923 A1 | 6/2018 |

OTHER PUBLICATIONS

Neculaes et al., "Multisource X-ray and CT: Lessons learned and Future outlook," IEEE Speical section on Emerging Computed Tomography Technologies, vol. 2, pp. 1568-1585. (Year: 2014).*

(Continued)

*Primary Examiner* — Kiho Kim
(74) *Attorney, Agent, or Firm* — Gowling WLG (Canada) LLP

(57) ABSTRACT

A computed tomography (CT) scanning apparatus that includes a set of X-ray sources and a set of flat panel detectors with a set of source collimators and a set of detector collimators therebetween. The design of the openings of the set of detector collimators is such that the images received by the set of flat panel detectors may be combined, or stitched together to generate a single X-ray image.

16 Claims, 13 Drawing Sheets

(51) Int. Cl.
  *A61B 6/08*     (2006.01)
  *A61B 6/40*     (2024.01)
  *A61B 6/42*     (2024.01)

(58) Field of Classification Search
  CPC ... A61B 6/4233; A61B 6/4441; A61B 6/4085;
  G01N 23/046
  See application file for complete search history.

(56) References Cited

U.S. PATENT DOCUMENTS

| | | |
|---|---|---|
| 2010/0246753 A1 | 9/2010 | Mollov |
| 2012/0063565 A1* | 3/2012 | Klingenbeck .......... A61B 6/488 378/9 |
| 2012/0201349 A1 | 8/2012 | Kaneko et al. |
| 2012/0328072 A1 | 12/2012 | Shi et al. |
| 2015/0071402 A1 | 3/2015 | Handa |
| 2017/0348547 A1 | 12/2017 | Lee et al. |
| 2018/0125438 A1* | 5/2018 | Lauritsch ............. A61B 6/5205 |
| 2019/0099136 A1* | 4/2019 | Ogata .................. A61B 6/06 |

OTHER PUBLICATIONS

Cao et al., "A stationary-sources and rotating-detectors Computed Tomography Architecture for Higher Temporal Resolution and Lower Radiation Dose", IEEE Speical section on Emerging Computed Tomography Technologies, vol. 2, pp. 1263-1271. (Year: 2014).*

The International Search Report for the corresponding PCT Application No. PCT/CA2020/050693 dated Aug. 21, 2020.

* cited by examiner

Figure 4e
Figure 4f

METHOD AND APPARATUS FOR FLAT PANEL COMPUTED TOMOGRAPHY

CROSS-REFERENCE TO OTHER APPLICATIONS

The current application claims priority from U.S. Provisional Application No. 62/851,894 filed May 23, 2019 which is hereby incorporated by reference.

FIELD

The disclosure is generally directed at X-ray imaging and, more specifically, at a method and apparatus for flat panel computed tomography.

BACKGROUND

Conventional computed tomography (CT) systems are quite popular for both medical and industrial use but suffer from fixed footprints and poor spatial resolution. On the other hand, emerging CT systems based on large area flat panel detectors are increasingly finding use in medical (e.g. radiotherapy and extremity imaging), security (e.g. baggage inspection at airports), industrial (e.g. non-destructive test of large automotive parts) and veterinary (e.g. animal imaging) applications. Some advantages of flat panel CT over traditional CT include the increased portability of the flat panel imaging system, lower system costs, finer spatial resolution of flat panel devices and larger scan areas due to their 43 cm×43 cm flat panel size.

Currently flat panel CT systems typically use the same system design as conventional CT where the detector array is simply replaced with a large area flat panel detector. In addition, the fan beam is changed to a cone beam to increase the scan area. However, flat panel CT has not been able to compete well with conventional CT in many applications due to its worse image quality. One of the reasons is the lower scan speed of flat panel detectors which is limited by the higher spatial resolution, Cesium Iodide, scintillator commonly used in flat panel detectors that suffers from afterglow and the limited mobility of amorphous and polycrystalline semiconductors used for large area flat panel detector readout electronics. Lower scan speeds make the cone beam CT susceptible to artifacts from object motion. Although the scan speeds for modern full size (43 cm×43 cm) flat panel detectors are about 30 fps at full spatial resolution (e.g. 150 um), the speed can be improved if pixel binning is applied to trade-off image resolution for speed.

Another reason as to why flat panel CT falls behind conventional CT is due to excess object dependent scatter noise in the image. In a conventional CT imaging system, a fan beam is used to reduce scatter by reducing the scanning volume of the beam whereas using a fan beam X-ray source is not pragmatic for flat-panel CT because it further reduces the scan speed of the slower flat panel detectors.

Therefore, there is provided a novel method and apparatus for flat panel CT imaging.

SUMMARY

Accordingly, there is a need for a flat panel CT imaging system that can provide image quality approaching conventional CT imaging equipment while maintaining the advantages of portability and lower costs.

In one aspect, there is provided a computed tomography (CT) scanning apparatus including at least two X-ray sources for generating X-ray beams; at least two flat panel X-ray detectors, wherein each of the at least two flat panel X-ray detectors is associated with one of the at least two X-ray sources, the number of flat panel X-ray detectors equal to the number of X-ray sources; a set of X-ray source collimators for collimating the X-ray beams from the at least two X-ray sources; and a set of detector collimators for collimating the X-ray beams prior to the X-ray beams reaching the at least two flat panel X-ray detectors.

In another aspect, the set of detector collimators equals the number of flat panel X-ray detectors. In a further aspect, each of the set of detector collimators includes at least one detector collimator opening. In yet another aspect, a combination of all of the detector collimator openings of the set of detector collimators equal a surface of the flat panel X-ray detectors. In yet another aspect, the at least two X-ray sources include a thermionic emission source or a cold cathode source.

In an aspect, the apparatus further includes a gantry ring where the at least two X-ray sources, the at least two flat panel X-ray detectors, the set of X-ray source collimators and the set of detector collimators are mounted. In a further aspect, the apparatus further includes a set of stationary rings where the at least two X-ray sources and the at least two flat panel X-ray detectors are mounted; and a rotational ring where the set of X-ray source collimators and the set of detector collimators are mounted. In another aspect, the apparatus further comprises a processor for combining images received by the set of flat panel X-ray detectors into a full X-ray image. In yet a further aspect, the set of flat panel X-ray detectors is a set of tiled flat panel detectors. In another aspect, the set of flat panel X-ray detectors are a set of rigid flat panel X-ray detectors or a set of flexible flat panel X-ray detectors. In yet another aspect, the at least one detector collimator opening for each of the set of detector collimators is offset from the at least one detector collimator openings for the other of the set of detector collimators. In an aspect, the at least one detector collimator openings for each of the set of detector collimators combine with the at least one detector collimator openings for each of the other of the set of detector collimators to equal a surface area of a flat panel X-ray detector.

In another aspect of the disclosure, there is provided a method of computed tomography (CT) scanning including directing a set of X-ray beams from a set of X-ray sources towards a set of flat panel X-ray detectors; collimating the set of X-ray beams via a set of detector collimators before the X-ray beams reach the set of flat panel X-ray detectors; and combining images generated by the set of flat panel X-ray detectors into a full X-ray image.

In an aspect, the method further includes collimating the set of X-ray beams via a set of source collimators before collimating the set of X-ray beams via the set of detector collimators. In a further aspect, the method includes collimating the set of X-ray beams via the set of source collimators includes collimating the X-ray beams into a set of fan beam X-rays. In yet a further aspect, the set of detector collimators include openings that when combined equal a surface area of the flat panel X-ray detector.

In yet a further aspect of the disclosure, there is provided a computed tomography (CT) scanning apparatus including at least one stationary X-ray source for generating X-ray beams; a stationary circular ring of flat panel X-ray detectors for receiving the X-ray beams; and a rotating ring including: a set of X-ray source collimators for collimating the X-ray beams from the at least one stationary X-ray source; and a set of detector collimators for collimating the X-ray beams prior to the X-ray beams reaching the stationary circular ring of flat panel X-ray detectors.

BRIEF DESCRIPTION OF THE DRAWINGS

Embodiments of the present disclosure will now be described, by way of example only, with reference to the attached Figures.

FIG. 4b is a schematic view of the combined openings of the set of detector collimators of FIG. 4a;

FIG. 4e is a schematic diagram of another embodiment of a set of detector collimators;

FIG. 4f is a schematic diagram of yet another embodiment of a set of detector collimators;

DETAILED DESCRIPTION OF THE EMBODIMENTS

The disclosure is directed at a method and system for flat panel computed tomography (CT). In one embodiment, the system of the disclosure includes a set of X-ray sources and a set of flat panel detectors (FPD) for detecting X-rays that are transmitted by the set of X-ray sources. The system further includes a set of X-ray source collimators and a set of FPD, or detector, collimators that assist to collimate, or direct, the X-rays transmitted by the set of X-ray sources and to collimate, or direct, the X-ray beams received by the set of FPD, respectively.

Figure 1:
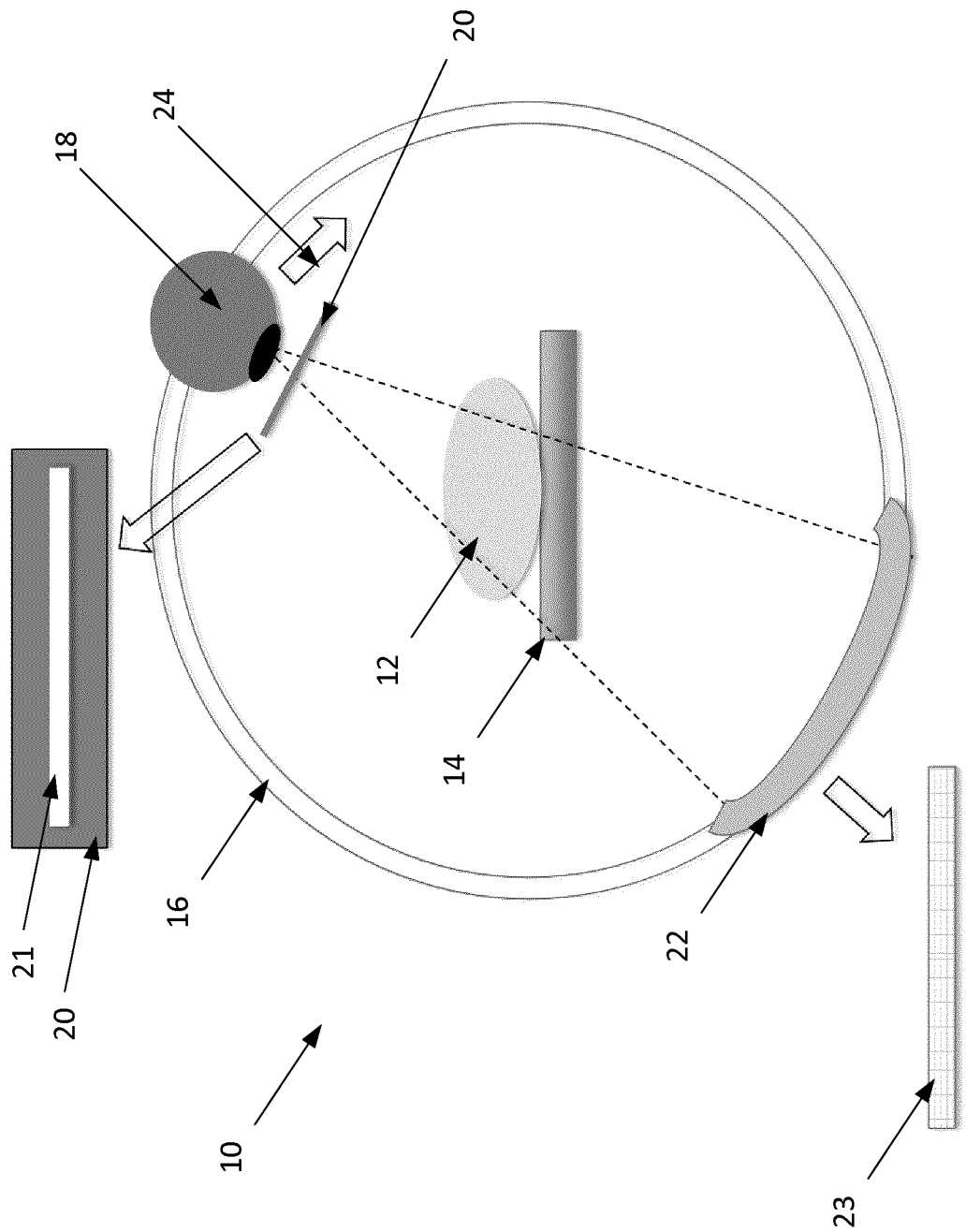
FIG. 1 is a schematic front view of a prior art computed tomography (CT) imaging system.
Figure 2:
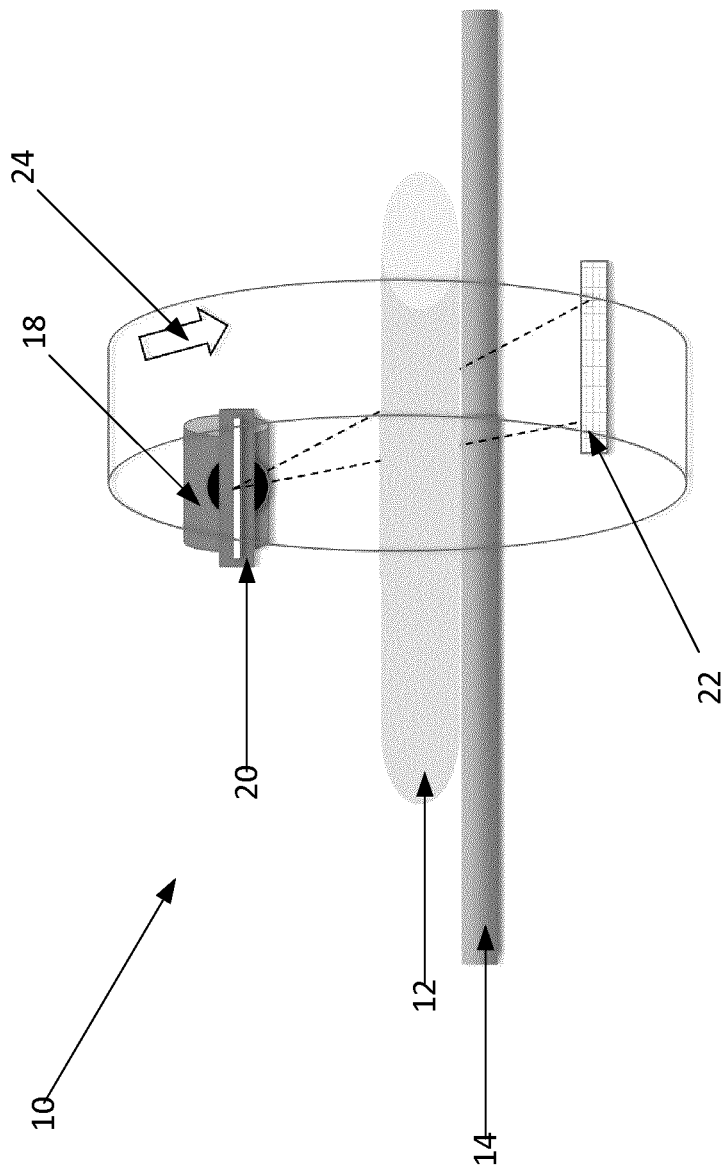
FIG. 2 is a schematic side view of the CT system of FIG. 1.

Turning to FIGS. 1 and 2, front and side schematic views of a conventional fan beam CT apparatus are shown. The CT apparatus 10 is used to examine an object of interest, such as a patient 12, that is lying on a table 14 in the middle of the CT apparatus 10. The CT apparatus includes a single ring gantry 16 that holds an X-ray source 18, seen as an X-ray tube, an X-ray source collimator 20, seen as a fan beam collimator, and a detector array 22 or flat panel detector (FPD). An enlarged view of the X-ray source collimator 20 is also shown as part of FIG. 1 along with a schematic diagram of a front 23 of the detector array 22. The fan beam, or source, collimator 20 includes an opening 21 that reduces the beam area of the X-ray beam provided by the X-ray source 18 such that the fan beam only covers the detector array 22 enabling object scatter rejection. In operation, the gantry 16 rotates (such in the direction of arrow 24) about the patient 12 and table 14 at a high speed (typically 1 s or less) to acquire many image slices from multiple projection angles that are then reconstructed into a 3D volumetric image.

Conventional flat panel cone-beam CT imaging equipment typically uses at least 300 projections to achieve acceptable reconstruction due to the high noise in the FPD that diminishes any improvement offered by more projections. This number of 300 projections is lower than the 1000 projections typically used in conventional CT equipment. Acquiring 300 projections can take up to 10 seconds with a flat panel detector cone beam CT system if the flat panel detector is operated at 30 fps but speed improvements are possible with binning.

Figure 3A:
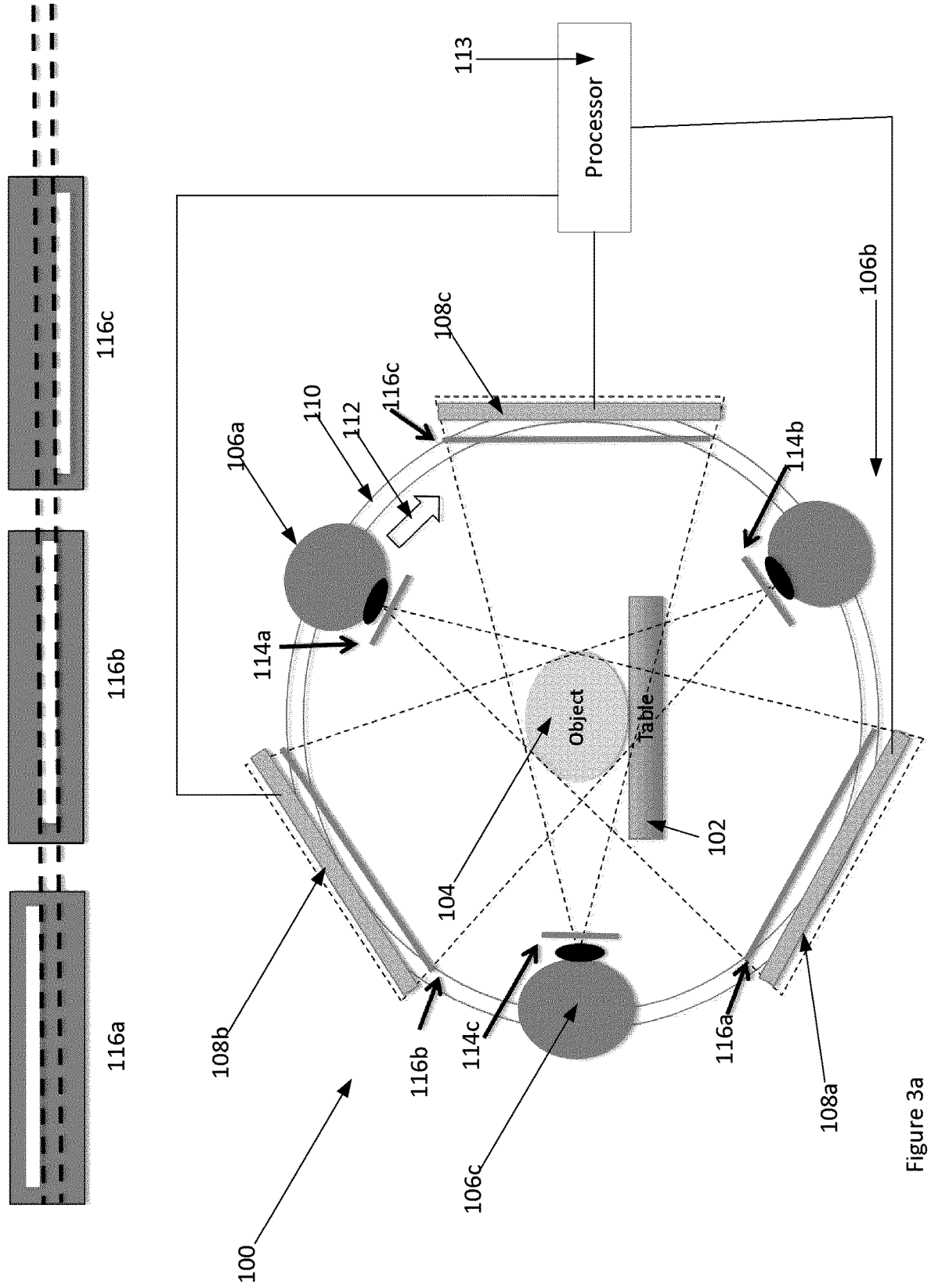
FIG. 3a is a schematic view of a first embodiment of a CT imaging system in accordance with the current disclosure.

Turning to FIG. 3a, a schematic diagram of a CT imaging, or scanning, system in accordance with the disclosure is shown. The system 100 includes a table 102 atop which an object of interest, such as a patient 104, that is being scanned lies. The system 100 further includes a set of X-ray sources 106, seen in the present embodiment as X-ray source #1 106a, X-ray source #2 106b and X-ray source #3 106c and a set of FPDs 108 (seen as FPD #1 108a, FPD #2 108b and FPD #3 108c) with X-ray source "n" associated with FPD "n" for the present embodiment. The X-ray sources 106 and the FPD 108 are mounted to a gantry ring 110 that rotates around the patient 104, such as in the direction of arrow 112. Alternatively, the gantry ring 110 may rotate in the opposite direction. While three X-ray sources 106 and three FPDs 108 are shown in the current embodiment, systems 100 including at least two X-ray sources 106 and at least two FPDs 108 are contemplated to increase the readout speed of the CT imaging system. The system may further include a processor 113 for controlling the X-ray sources 106 and the FPDs 108 and for receiving the images generated by the FPDs 108.

In front of each X-ray source 106 is an X-ray source collimator 114 while in front of each FPD 108 is a detector, or FPD, collimator 116. Each collimator 114 and 116 include openings, or slits, enabling the X-rays to pass through the collimators 114 and 116 as they travel from the X-ray source 106 to the FPD 108. Each X-ray source collimator 114 collimates the X-ray beams that are emitted by its associated X-ray source. In one embodiment, the X-ray beams are collimated into a fan beam shape. This is schematically shown in FIG. 3a via the dotted lines extending from each X-ray source 106 to its associated X-ray detector 108. Each detector collimator 116 receives the fan beam X-rays and then further collimates the beams and directs them toward its associated FPD 108, or detector array. Use of the detector collimators enables a reduction in scatter which improves a final image that is reviewed by a user.

In one embodiment, a design of the X-ray source collimator 114n (where "n" represents one of the sets of X-ray source and FPD pairs) aligns and mirrors with a design of the FPD collimator 116n whereby the openings within associated collimator pairs are similar and account for any magnification or demagnification effects.

As shown at a top of FIG. 3a, the three detector collimators 116 are shown. It is understood in one embodiment, the surface area of the detector collimator is approximately the same as the area of the detector array within the FPD 118. In this embodiment, it can be seen that openings of the three detector collimators 116 are offset with respect to each other so that each X-ray source and detector pair acquires approximately only one third of the full sized flat panel image in one projection. In the current embodiment, the slit, or opening, in the detector collimator 116a associated with X-ray source #1 106a and FPD #1 108a is located at a top portion of the detector collimator 116a, the slit, or opening, in the detector collimator 116b associated with X-ray source #2 106b and FPD #2 108b is located in a middle portion of the detector collimator 116b and the slit, or opening, in the detector collimator 116c associated with X-ray source #3 106c and FPD #3 108c is located in a bottom portion of the detector collimator 116c. Once all images are acquired, the sub-images (or images collected by each of the FPDs 108) can be algorithmically corrected and stitched to create full projections. If necessary, there can be some overlap between the images to allow for proper alignment and stitching.

An advantage of this disclosure is that since the exposed detector area for each FPD is reduced (in the current embodiment, ⅓ that of a typical cone beam system), scatter related noise can be reduced leading to improved image quality. For the implementation shown in FIG. 3a, 300 projections are acquired in the same time as a conventional flat panel cone beam CT system (e.g. 10 seconds if the detectors can be read out at 30 fps), however the image quality is improved due to the reduced scatter. If a further increase in imaging speed and/or scatter reduction is required, additional X-ray sources, X-ray source collimators, detectors and offset detector collimators combinations can be added.

As outlined above, in this embodiment, the X-ray source collimators are aligned with their associated detector collimators such that the beams from the respective X-ray sources reach their respective detector through the detector collimator. In the current embodiment, the X-ray sources 106 only direct or emit X-ray beams toward their associated FPD 108.

In the current embodiment, the set of X-ray sources 106 are mounted to the gantry ring 110 equidistance apart from each other. Similarly, the set of FPDs 108 are also mounted to the gantry ring 110 equidistance apart from each other directly across from its associated X-ray source. In the current embodiment, each one of the set of FPDs 108 is associated with only one of the set of X-ray sources, however other ratios between FPDs and X-ray sources are possible as discussed below. Alternatively, the set of X-ray sources and the set of FPDs may not be mounted equidistance apart from each other in the set but X-ray source and FPD pairs are mounted across from each other on the gantry ring.

Figure 3B:
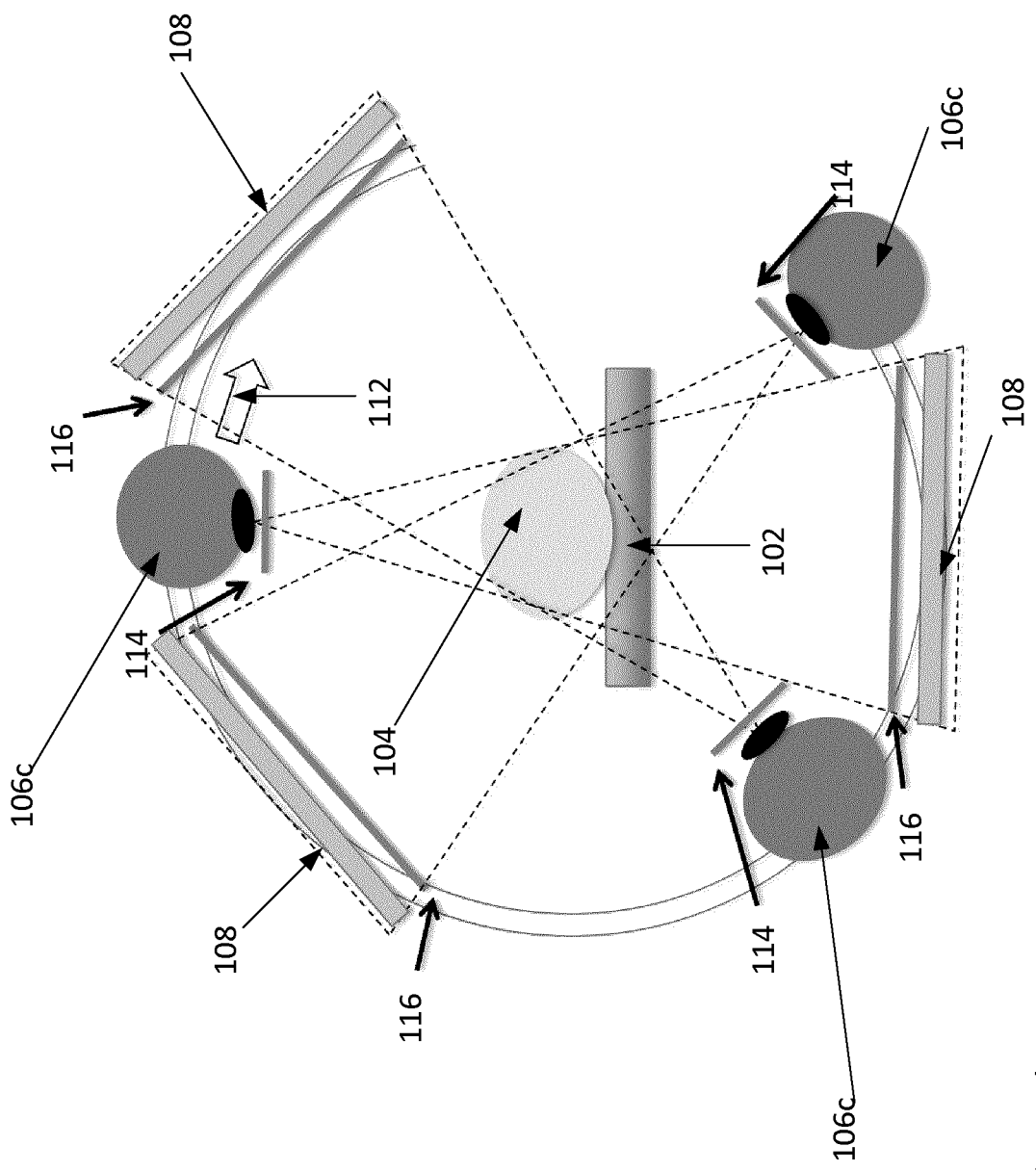
FIG. 3b is a schematic view of another embodiment of a CT imaging system in accordance with the current disclosure.

Turning to FIG. 3b, a schematic diagram of another embodiment of a CT imaging, or scanning, system is shown. As shown in FIG. 3b, the set of X-ray sources 106 and the FPDs 108 are mounted on a C-arm structure 120 instead of a gantry ring. In this manner, the spacing between the X-ray sources in the set of X-ray sources 106 and the FPDs 108 in the set of FPDs is reduced due to the shape of the C-arm structure 120, however operation of the CT imaging system is similar to the embodiment described with respect to FIG. 3a. In operation, as the C-arm structure rotates, the X-ray sources 106 direct X-rays or X-ray beams through the source collimators 114 and the detector collimators 116 toward their associated FPD 108. As with the embodiment of FIG. 3a, the design of the openings within the set of detector collimators 116a is such that the exposed detector area is reduced for each detector but that the resulting images can be combined to generate a full image with some further processing or manipulation after the scanning has completed.

Figure 4A:
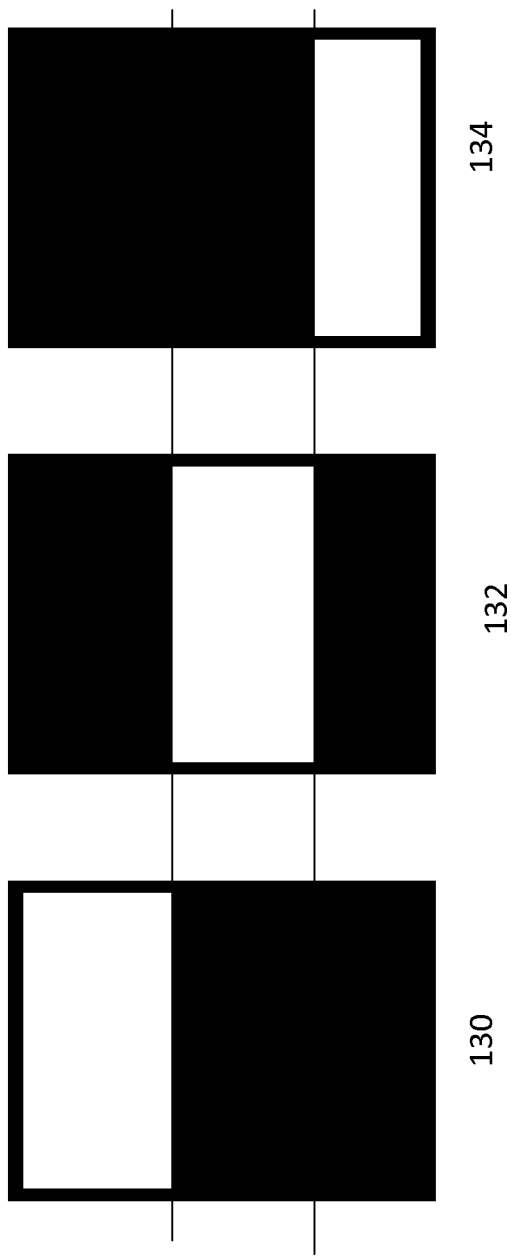
FIG. 4a is a schematic view of a first embodiment of a set of detector collimators.
Figure 4B:
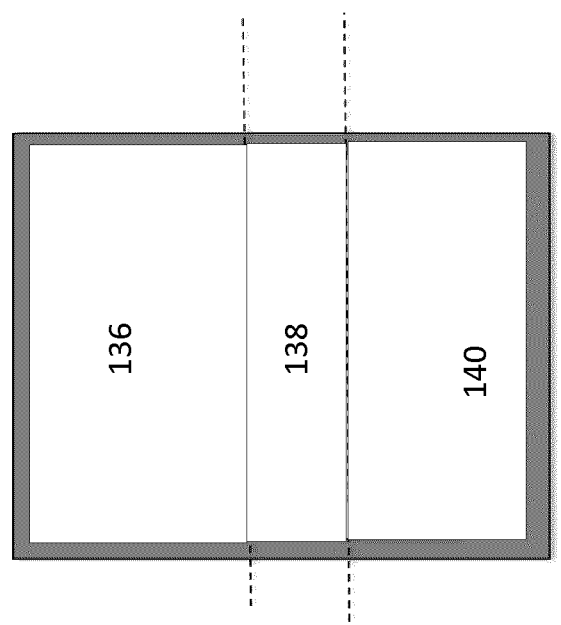

Turning to FIG. 4a, a first embodiment of a set of three detector collimators is shown. This design is similar to the design shown in FIG. 3a. As can be seen in FIG. 4a, the opening in a first detector collimator 130 is at a top portion of the detector collimator, the opening in a second detector collimator 132 is at a middle portion of the collimator and the opening in a third detector collimator 134 is at a bottom portion of the collimator. In operation, the fan beamed X-rays from their respective X-ray sources pass through the openings and generate an image on the associated FPD. When the images from the set of FPDs are combined together with a first detector image 136 from the first detector (seen as the first detector collimator 130), a second detector image 138 from the second detector (seen as the second detector collimator 132) and a third detector image 140 from the third detector (seen as the third detector collimator 134), a full image may be generated as shown FIG. 4b. The collimator openings can be aligned with each other as shown by the dotted lines with some overlap, if necessary, to help stitch the final image.

Figure 4C:
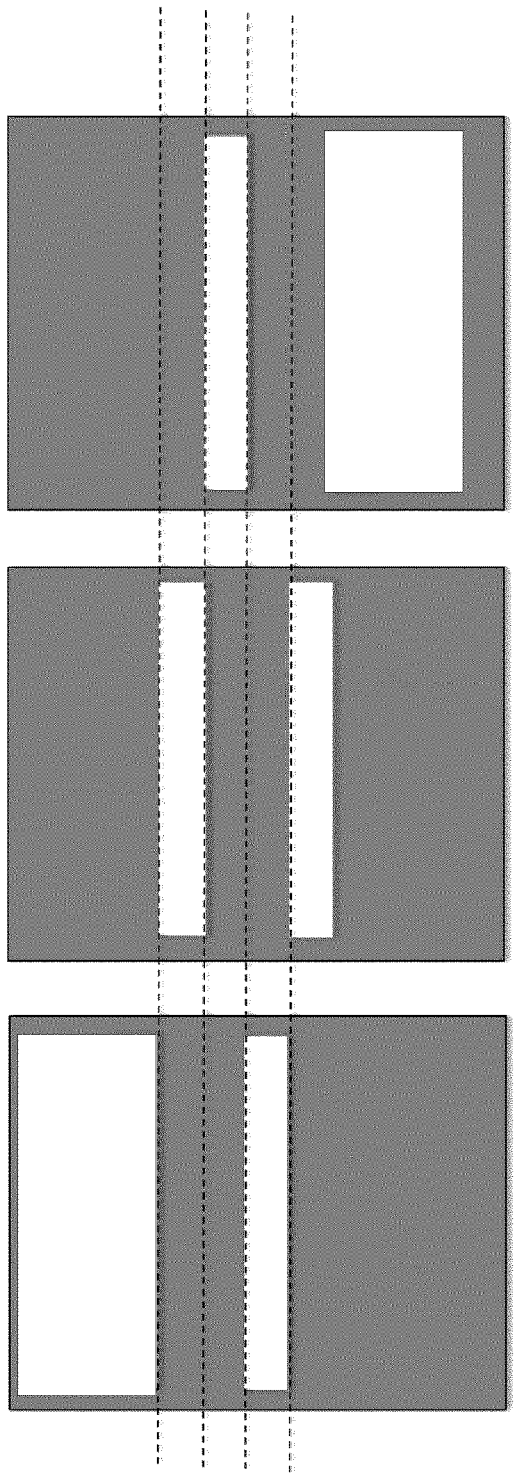
FIG. 4c is a schematic view of a second embodiment of a set of detector collimators.
Figure 4D:
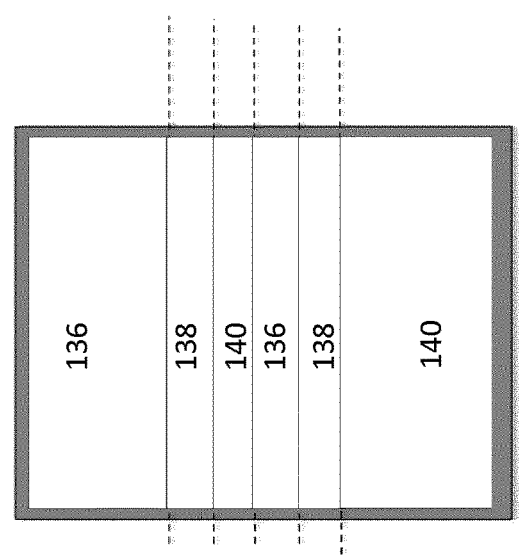
FIG. 4d is a schematic view of the combined openings of the set of detector collimators of FIG. 4c.
Figure 4G:
FIG. 4g is a schematic diagram of a further embodiment of a set of detector collimators.
Figure 4G:
Figure 4G:
Figure 4G:
Figure 4H:
FIG. 4h is a schematic diagram of yet a further embodiment of a set of detector collimators.
Figure 4H:
Figure 4H:
Figure 4H:
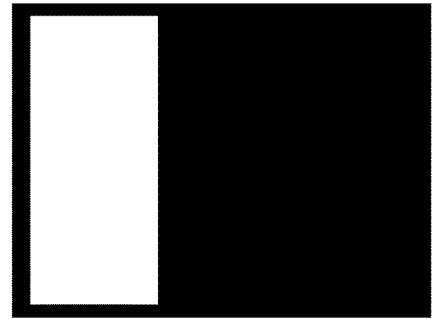

Turning to FIG. 4c, a second embodiment of a design for a set of three detector collimators is shown. It will be understood that the source collimators aligned with each of the detector collimators have a similar design in order to align the collimated X-ray beams (such as fan beams) from the X-ray source with the openings in the respective detector collimators. In the embodiment of FIG. 4c, with each of the detector collimators including more than one opening, narrower fan beams can be used or achieved without increasing the number of X-ray sources or detectors or reducing the collimated area to achieve even less scatter related noise. As with the embodiment of FIG. 4a, when the images 136, 138 and 140 generated by each of the set of FPDs are combined, a full image can be generated such as schematically shown in FIG. 4d. This is possible in the embodiment of FIG. 4c because the same total image area per source (i.e. approximately ⅓ of a full image) is exposed, however, the exposed area for each collimator or detector is separated into two smaller separated exposed areas in order to reduce scatter reaching the FPD. It will be understood that the openings for each of the detector collimators does not need to be equal in size to each other.

As discussed above, for the detector collimators of FIG. 4c, the design of the source collimators is adapted so that two fan beams are generated from each X-ray source that align with the openings within each of the detector collimators. This may require adapting the physical location of the source collimator for example, by moving it further away from the source to get the right alignment. It can be understood that other designs of collimator openings for the detector collimators are possible. For instance, squares placed in a grid instead of horizontal slits can be utilized to improve the reduction in scatter without increasing the number of X-ray sources and/or detectors. By designing the totality or sum of the openings in each of the detectors collimators to equal a surface area of the FPD array, or screen, this may be achieved.

In some embodiments, such as for a set of three detector collimators, the first detector collimator may have an opening that is ⅔ of the detector array while the second and third detector collimators may have openings that are ⅙ of the detector array. Other examples of detector collimator designs are shown in FIGS. 4e to 4h. It will be understood that there is no limit to the number of detector collimators but that it may be dictated from an engineering or manufacturing standpoint.

With respect to the X-ray sources, stationary X-ray sources such as carbon nanotube (CNT) based field emitters may also be used instead of thermionic X-ray tubes with system and method of the disclosure. Use of multi-source CNT type arrays can help reduce or eliminate the need for multi-slit source collimators since these X-ray sources can be turned on and off as required. Use of CNT sources can also serve to make the X-ray system lightweight, more portable and immune to vibration.

Figure 5:
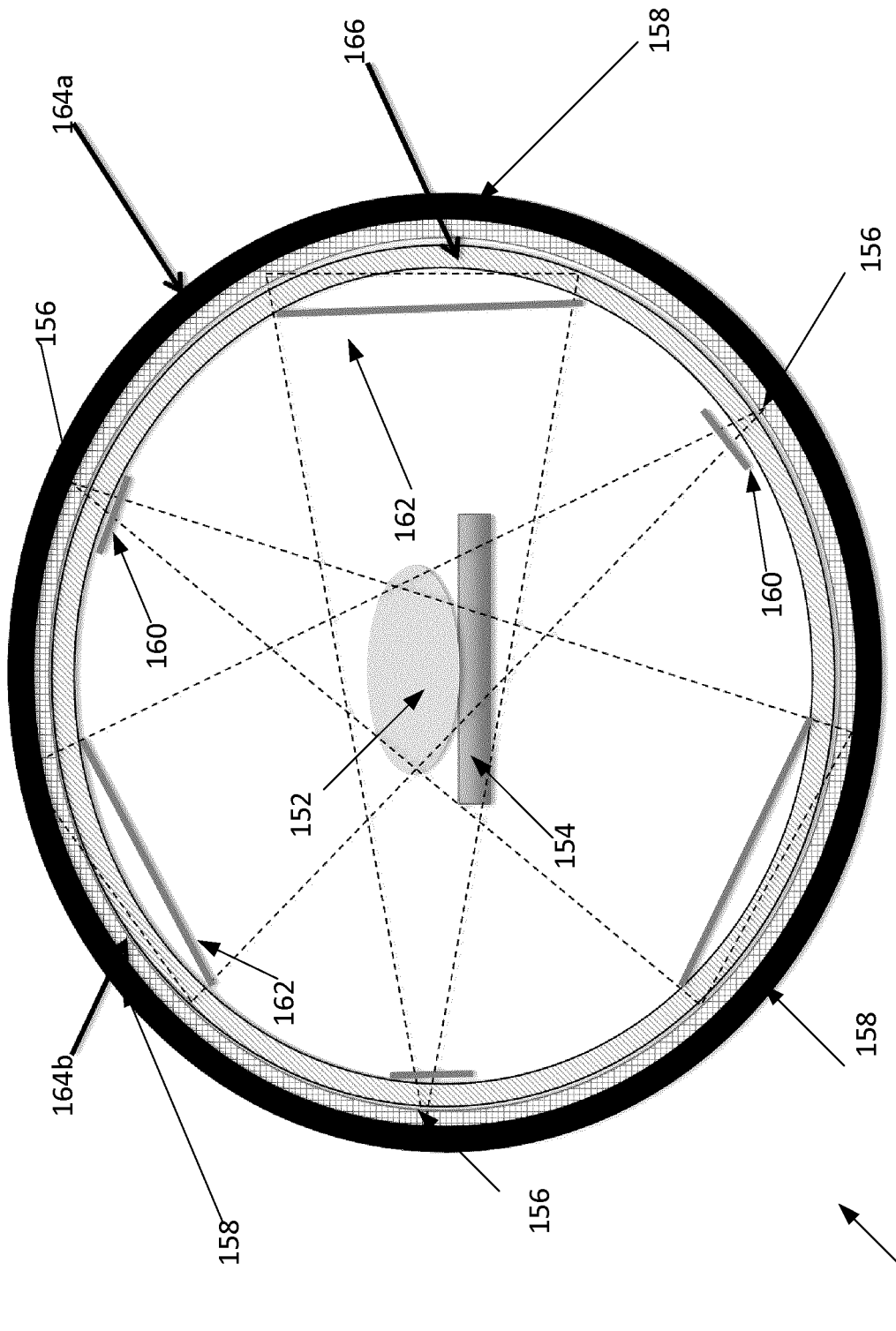
FIG. 5 is a schematic front view of yet another embodiment of a CT imaging system in accordance with the current disclosure.
Figure 6:
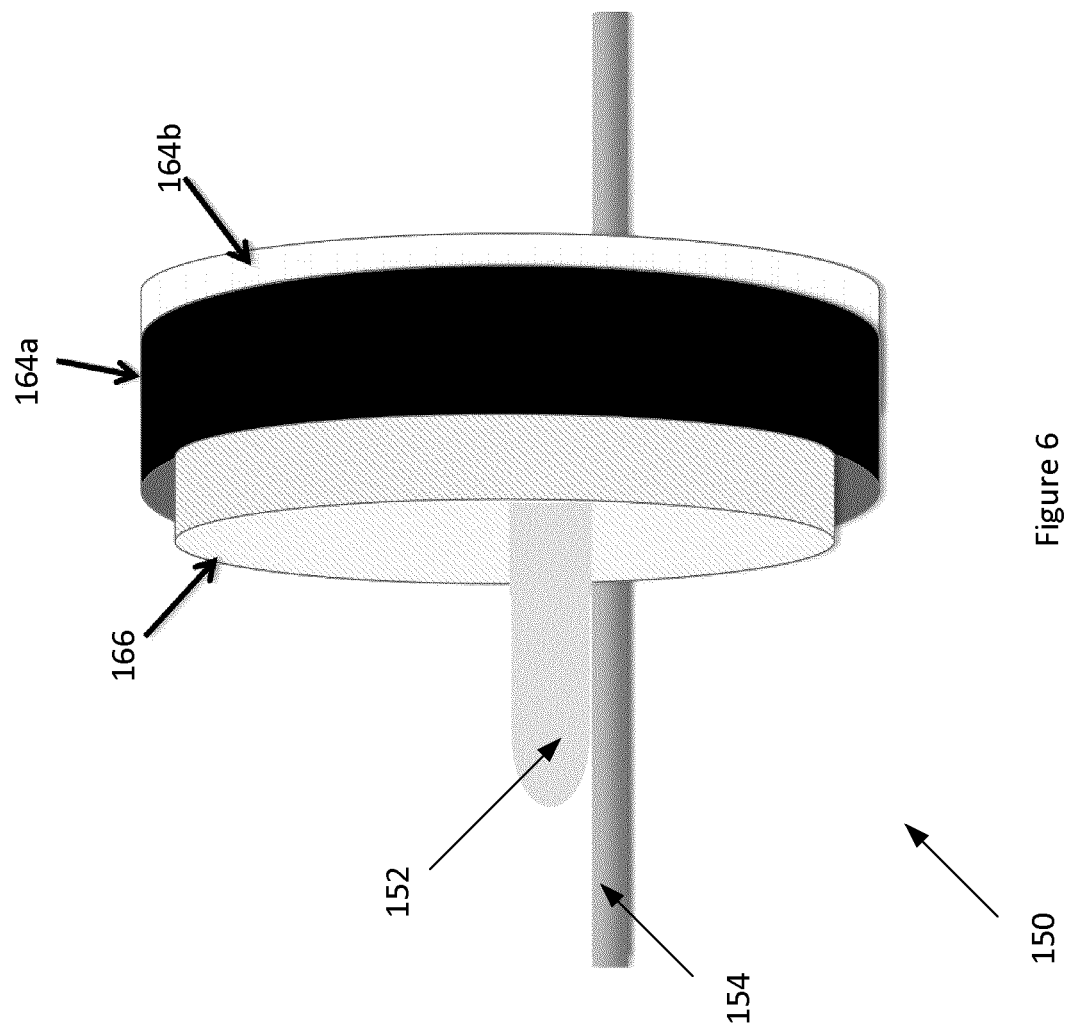
FIG. 6 is a schematic side view of the CT imaging system of FIG. 5.

Turning to FIGS. 5 and 6, schematic diagrams of a further embodiment of a CT scanning apparatus is shown. In the current embodiment, the CT apparatus 150 is used to image an object of interest 152 that is resting on a platform, or table, 154 in the middle of the CT imaging apparatus 150. As with the previous embodiments, the CT apparatus 150 includes a set of X-ray sources 156, a set of FPDs 158, a set of source collimators 160 and a set of detector collimators 162. The CT apparatus 150 further includes a pair of stationary rings 164 with one of the stationary rings 164a including the set of FPDs and the other stationary ring 164b housing a set of X-ray sources, such as, but not limited to, multi-source CNT type arrays. In one embodiment, the stationary ring 164b may be a single ring of X-ray sources and the stationary ring 164a may be a single ring of tiled FPDs whereby an inner surface of the stationary rings 164a and 164b are covered by FPDs and X-ray sources, respectively. A third rotational ring 166 preferably includes the set of source collimators 160 and the set of detector collimators 162 where each of the set of source collimators aligns with one of the set of detector collimators such as discussed above.

In operation, after the X-ray sources 156 are initiated, triggered, or turned on, the rotational ring 166 rotates thereby enabling images to be captured by the set of FPDs 158 and to improve scatter rejection. In the current embodiment, the CT apparatus, or system 150, may enable high quality scatter noise free images, fast acquisition and greater portability. Although a design of the detector collimators is not shown, it will be understood that the openings in the set of detector collimators represent a surface area of the flat panel display such as discussed above. In one embodiment of FIG. 5, three different X-ray arrays within each X-ray source 156 (which may be a multi-source CNT array) are triggered simultaneously to acquire three projection images simultaneously.

In one embodiment, one manner of timing for the set of X-ray sources is to trigger each CNT, or X-ray, source 156 in sequence and to synchronize the rotating ring 166 so that the associated source and detector collimators are in line with the X-ray source(s) being triggered. The detectors or FPDs on the stationary outer ring 164a are preferably tiled and/or overlapped to reduce gaps at the tiling seams. Alternately, larger roll-to-roll flexible X-ray detectors that can extend to cover larger areas (including up to the complete outer stationary ring 164a without need for tiling) can be employed to reduce issues with tiling. In another embodiment of this disclosure, the X-ray sources 156 can timed and pulsed to avoid exposing the seams and/or tiling gaps if any exist.

Figure 7:
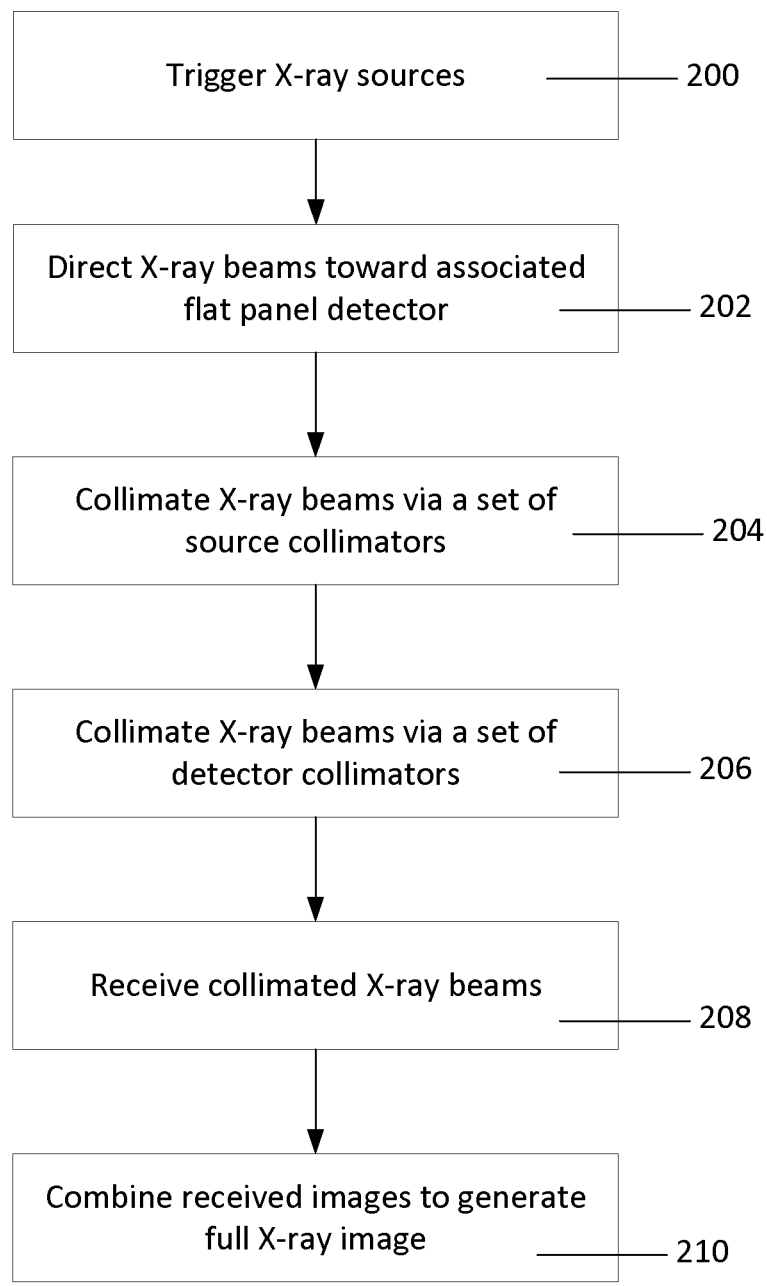
FIG. 7 is a flowchart outlining a method of CT imaging.

Turning to FIG. 7, a flowchart outlining a method of CT imaging is shown. Initially, the X-ray sources are triggered or turned on (200). The X-ray beams of one X-ray source within a set of X-ray sources are then directed toward a flat panel detector (202) within a set of FPDs. In some embodiments, the X-ray sources and the FPDS are in a one to one relationship. In other embodiments, the X-ray source or sources may be directed at a tiled set of FPDs. The directed X-ray beams are then collimated by a source collimator (204). In one embodiment, the collimation of the directed X-ray beams may be into a fan beam shape although other shapes such as, but not limited to, grid defined beamlets or a set of adjacent cone beams are contemplated. The source collimator collimated, which may be fan beam shaped, X-rays are then collimated by a detector collimator (206) before the X-ray beams reach and are received by the FPD (208). The set of images that are received by the set of FPDs are then combined to generate a full X-ray image (210).

Figure 8:
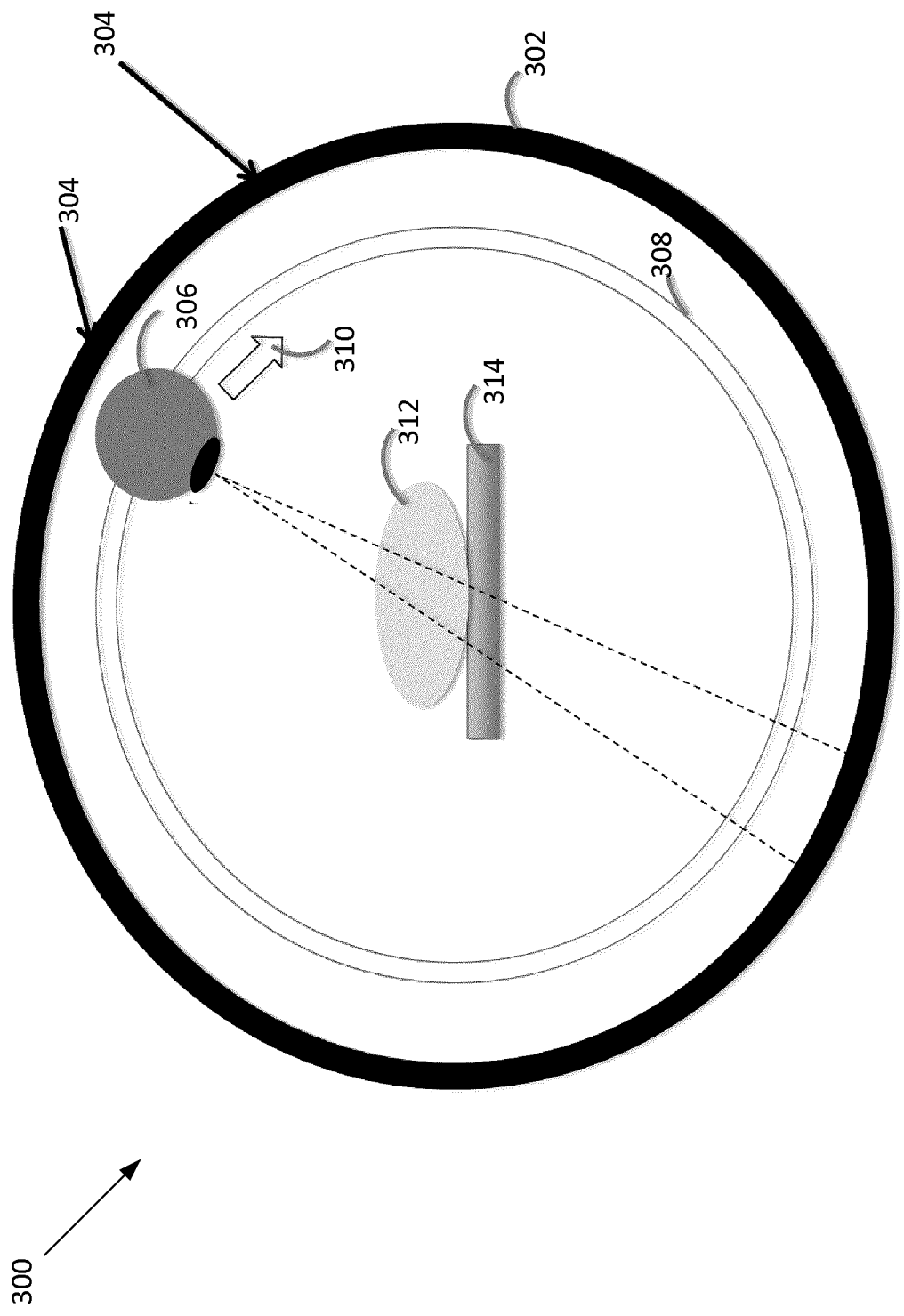
FIG. 8 is a schematic front view of yet another embodiment of a CT imaging system in accordance with the current disclosure.
Figure 9:
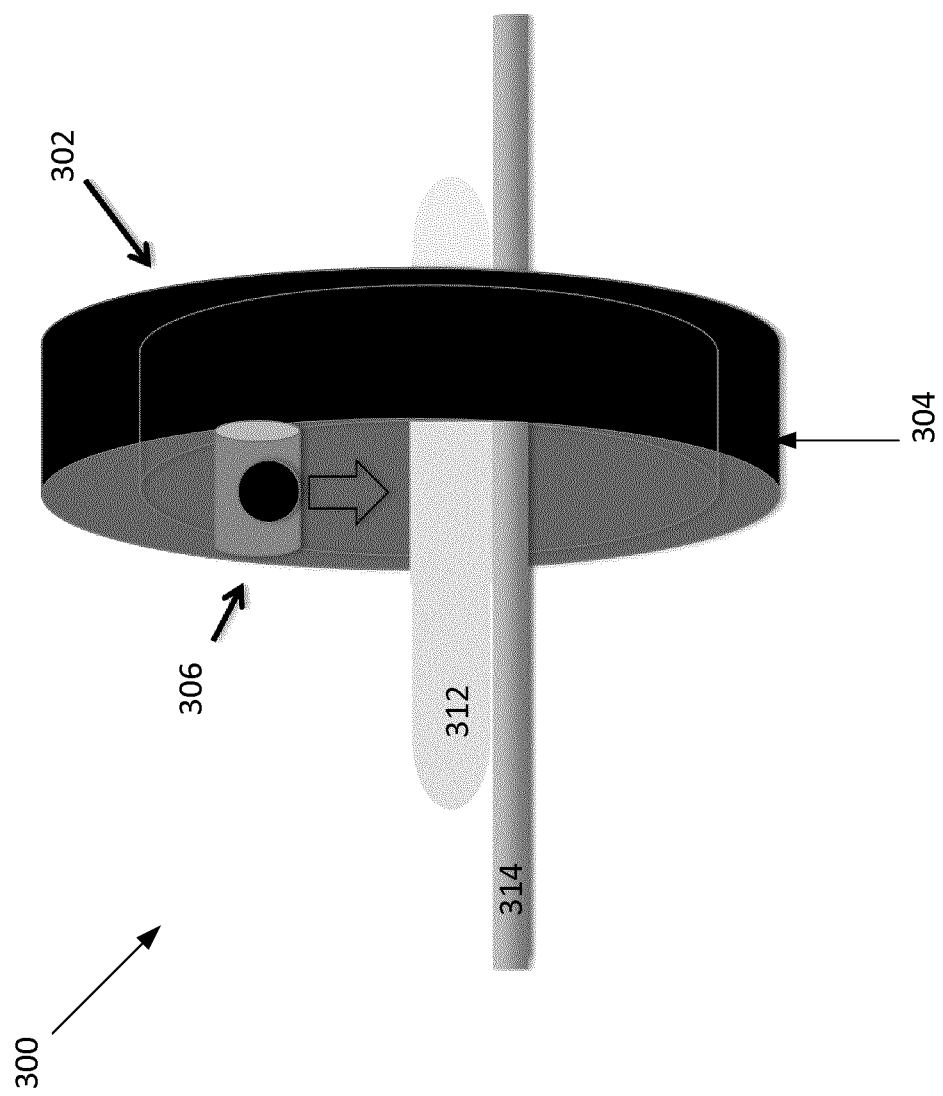
FIG. 9 is a schematic side view of the CT imaging system of FIG. 8.

Turning to FIGS. 8 and 9, another embodiment of a CT imaging system is shown. FIG. 8 shows a front view of the flat panel CT system while FIG. 9 provides a side view of the CT system. One advantage of the current embodiment is to overcome the scan speed limitation or limitations associated with large area flat panel X-ray detectors. The CT system 300 includes a stationary outer ring 302 including a set of tiled, curved flat panel X-ray detectors or FPDs 304. In the current embodiment, the flexible FPDs 304 cover an inside wall of the stationary outer ring 302. An X-ray source 306 is mounted on an inner ring 308 and rotated (such as in a clockwise direction as indicated by arrow 310) around a patient or object or interest 312 (on a table 314) to acquire the necessary projections for tomographic reconstruction. Alternatively, the X-ray source 306 can rotate in a counterclockwise direction.

In one specific embodiment of the CT apparatus of FIGS. 8 and 9, 300 projections can be acquired in about 1.25 seconds since, for an object 3212 to detector 304 distance of ~0.5 m (i.e. a CT bore of 1 m), eight curved FPDs 304 (43 cm×43 cm) can be tiled in the outer ring 302 to enable acquisition at a rate that is approximately 8× more than that achievable with a single flat panel X-ray detector.

Moreover, although curved glass detectors can be used, high quality large area X-ray detectors on flexible substrates are also considered thereby enabling a variety of curvatures for the FPDs to address different applications of the CT system.

It should be noted that it is not necessary to cover the entire outer ring 302 with FPDS 304 but that even 180 degree coverage may be sufficient for reasonable image quality. A 180 degree flat panel detector coverage on the outer ring 302 may also provide the added advantage of faster scans because the X-ray source would have to travel a shorter distance.

FIG. 9 shows a side view of the CT system of FIG. 8. Again, the X-ray tube 306 shown in the inner ring 308 can be moved in either direction and can be operated in pulsed or continuous mode for higher speed. In FIG. 9, some amount of collimation may be beneficial to avoid exposing the inner ring 308 during projections to reduce or minimize reconstruction artifacts. Alternately, the inner ring 308 may be made of an X-ray transparent material with low scatter to reduce or minimize artifacts. An additional solution to this problem would have the outer ring 302 be in the same plane as the inner ring 308 (i.e. both rings have the same diameter). If the depth of the outer ring 302 is made less than the depth of the inner ring 308, then there would be less collimation needed and the inner ring would not be exposed to the beam.

In another embodiment, the outer ring 302 and inner ring 308 could be combined into a single ring.

In an alternate embodiment, the X-ray source, or tube, 305 shown in FIGS. 8 and 9 may be replaced by other stationary X-ray source technologies such as, but not limited to, arrays of field emission cathodes, carbon nanotubes emitters, and the like, that can cover a larger area than a conventional X-ray tube. Use of large X-ray emitter arrays may enable faster scans due to the larger area coverage and also reduce or minimize X-ray source motion related vibrations.

The curved detector arrays on the outer ring can be tiled and/or overlapped to reduce or minimize gaps at the tiling seams. Alternately, larger roll-to-roll flexible X-ray detectors that can extend to cover larger areas including up to the complete outer ring without need for tiling can be employed to reduce issues with tiling.

If a further increase in speed is necessary, additional X-ray sources may be mounted on the inner ring to acquire multiple images simultaneously.

One advantage of some embodiments of the system of the disclosure is that the detectors in the outer ring are stationary with respect to the patient or object of interest. Current CT systems require the detectors to move about or rotate the patient.

Another advantage of the CT system of the disclosure is that it may be scaled to larger objects of interest by increasing the size of the rings and adding more sources and/or X-ray detectors. It can be understood by one skilled in the art that the number and size of X-ray detectors can be varied and optimized for the application (e.g. radiotherapy, extremity, pulmonary, or head imaging) of the CT system. Moreover, detectors on flexible substrates can be used as well thus rapidly enabling a variety of curvatures as necessitated by the contemplated applications of the CT system of the disclosure.

In addition, conventional or stationary sources can be designed to supply different X-ray energies or use different X-ray filtration for each source to obtain multi-energy (e.g. dual energy) X-ray images for tissue differentiation applications. Moreover, the flat panel detectors may be multi-layer flat panel X-ray detectors that are capable of energy separation in a single exposure.

The CT system of the disclosure may also be combined with other imaging modalities (e.g. MRI, PET, SPECT, ultrasound, digital X-ray) to yield a multi-modality imaging system. For instance, the CT system may be combined with a portable head and neck MR-CT device for use in trauma imaging e.g. to visualize concussions.

In the preceding description, for purposes of explanation, numerous details are set forth in order to provide a thorough understanding of the embodiments. However, it will be apparent to one skilled in the art that these specific details may not be required. In other instances, well-known structures may be shown in block diagram form in order not to obscure the understanding. For example, specific details are not provided as to whether the embodiments or elements thereof described herein are implemented as a software routine, hardware circuit, firmware, or a combination thereof.

Embodiments of the disclosure or elements thereof can be represented as a computer program product stored in a machine-readable medium (also referred to as a computer-readable medium, a processor-readable medium, or a computer usable medium having a computer-readable program code embodied therein). The machine-readable medium can be any suitable tangible, non-transitory medium, including magnetic, optical, or electrical storage medium including a diskette, compact disk read only memory (CD-ROM), memory device (volatile or non-volatile), or similar storage mechanism. The machine-readable medium can contain various sets of instructions, code sequences, configuration information, or other data, which, when executed, cause a processor to perform steps in a method according to an embodiment of the disclosure. Those of ordinary skill in the art will appreciate that other instructions and operations necessary to implement the described implementations can also be stored on the machine-readable medium. The instructions stored on the machine-readable medium can be executed by a processor or other suitable processing device, and can interface with circuitry to perform the described tasks.

The above-described embodiments are intended to be examples only. Alterations, modifications and variations can be effected to the particular embodiments by those of skill in the art without departing from the scope, which is defined solely by the claims appended hereto.

What is claimed is:

1. A computed tomography (CT) scanning apparatus comprising:
   at least two X-ray sources for generating X-ray beams;
   at least two flat panel X-ray detectors, wherein each of the at least two flat panel X-ray detectors is associated with one of the at least two X-ray sources, the number of flat panel X-ray detectors equal to the number of X-ray sources;
   a set of X-ray source collimators for collimating the X-ray beams from the at least two X-ray sources;
   a set of detector collimators for collimating the X-ray beams prior to the X-ray beams reaching the at least two flat panel X-ray detectors;
   a set of stationary rings where the at least two X-ray sources and the at least two flat panel X-ray detectors are mounted; and
   a rotational ring where the set of X-ray source collimators and the set of detector collimators are mounted.

2. The CT scanning apparatus of claim 1 wherein the set of detector collimators equals the number of flat panel X-ray detectors.

3. The CT scanning apparatus of claim 2 wherein each of the set of detector collimators comprise at least one detector collimator opening.

4. The CT scanning apparatus of claim 3 wherein a combination of all of the detector collimator openings of the set of detector collimators equal a surface of the flat panel X-ray detectors.

5. The CT scanning apparatus of claim 3 wherein the at least one detector collimator opening for each of the set of detector collimators is offset from the at least one detector collimator openings for the other of the set of detector collimators.

6. The CT scanning apparatus of claim 5 wherein the at least one detector collimator openings for each of the set of detector collimators combine with the at least one detector collimator openings for each of the other of the set of detector collimators to equal a surface area of a flat panel X-ray detector.

7. The CT scanning apparatus of claim 1 wherein the at least two X-ray sources comprise a thermionic emission source or a cold cathode source.

8. The CT scanning apparatus of claim 1 further comprising a gantry ring where the at least two X-ray sources, the at least two flat panel X-ray detectors, the set of X-ray source collimators and the set of detector collimators are mounted.

9. The CT scanning apparatus of claim 1 further comprising a processor for combining images received by the set of flat panel X-ray detectors into a full X-ray image.

10. The CT scanning apparatus of claim 1 wherein the set of flat panel X-ray detectors is a set of filed flat panel detectors.

11. The CT scanning apparatus of claim 1 wherein the set of flat panel X-ray detectors are a set of rigid flat panel X-ray detectors or a set of flexible flat panel X-ray detectors.

12. A method of computer tomography (CT) scanning comprising:
   directing a set of X-ray beams from a set of X-ray sources towards a set of flat panel X-ray detectors wherein the set of X-ray sources and the set of flat panel X-ray detectors are mounted to a set of stationary rings;
   collimating the set of X-ray beams via a set of detector collimators before the X-ray beams reach the set of flat panel X-ray detectors wherein the set of detector collimators are mounted to a rotational ring; and
   combining images generated by set of flat panel X-ray detectors into a full X-ray image.

13. The method of claim 12 further comprising:
   collimating the set of X-ray beams via a set of source collimators before collimating the set of X-ray beams via the set of detector collimators.

14. The method of claim 13 wherein collimating the set of X-ray beams via the set of source collimators comprises:
   collimating the X-ray beams into a set of fan beam X-rays.

15. The method of claim 12 wherein the set of detector collimators comprise openings that when combined equal a surface area of the flat panel X-ray detector.

16. A computed tomography (CT) scanning apparatus comprising:
   at least one stationary X-ray source for generating X-ray beams;
   a stationary circular ring of flat panel X-ray detectors for receiving the X-ray beams; and
   a rotating ring including:
      a set of X-ray source collimators for collimating the X-ray beams from the at least one stationary X-ray source; and
      a set of detector collimators for collimating the X-ray beams prior to the X-ray beams reaching the stationary circular ring of flat panel X-ray detectors.

* * * * *